United States Patent
Grodzki

(10) Patent No.: US 9,696,399 B2
(45) Date of Patent: Jul. 4, 2017

(54) METHOD AND MAGNETIC RESONANCE APPARATUS FOR IMAGE ACQUISITION

(71) Applicant: David Grodzki, Erlangen (DE)

(72) Inventor: David Grodzki, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 760 days.

(21) Appl. No.: 14/050,580

(22) Filed: Oct. 10, 2013

(65) Prior Publication Data

US 2014/0097840 A1    Apr. 10, 2014

(30) Foreign Application Priority Data

Oct. 10, 2012 (DE) .................. 10 2012 218 424

(51) Int. Cl.
| | |
|---|---|
| G01V 3/00 | (2006.01) |
| G01R 33/48 | (2006.01) |
| G01R 33/56 | (2006.01) |
| A61B 5/055 | (2006.01) |

(52) U.S. Cl.
CPC ........ *G01R 33/482* (2013.01); *G01R 33/4816* (2013.01); *G01R 33/5602* (2013.01); *A61B 5/055* (2013.01)

(58) Field of Classification Search
CPC .............. G01R 33/482; G01R 33/4816; G01R 33/5602; A61B 5/055
USPC ....................................................... 324/312
See application file for complete search history.

(56) References Cited

U.S. PATENT DOCUMENTS

| | | | | |
|---|---|---|---|---|
| 4,818,940 A | * | 4/1989 | Hennig | G01R 33/5615 324/307 |
| 5,122,747 A | * | 6/1992 | Riederer | G01R 33/4822 324/309 |
| 5,446,384 A | * | 8/1995 | Dumoulin | G01R 33/4828 324/307 |

(Continued)

FOREIGN PATENT DOCUMENTS

JP          10286246 A     * 10/1998

OTHER PUBLICATIONS

Grodzki e tal., "Ultrashort Echo Time Imaging Using Pointwise Encoding Time Reduction With Radial Acquisition", Magn Reson Med, 67: pp. 510-518, Feb. 2012, published online Jun. 2011.*

(Continued)

*Primary Examiner* — Susan Lee
(74) *Attorney, Agent, or Firm* — Schiff Hardin LLP

(57) ABSTRACT

In a method and magnetic resonance apparatus for image acquisition using a magnetic resonance sequence in which k-space corresponding to the imaging area is scanned, a first region of k-space, which does not include the center of k-space, is scanned radially along a number of spokes emanating from the k-space center, and at least two phase coding gradients are completely ramped up before the excitation pulse. A second central region of k-space, which remains without the first region, is scanned in a Cartesian manner. For contrast increase a pre-pulse is provided before a predetermined number of individual measurements. The number of spokes is selected so a measurement point nearest to the k-space center is measured at a predetermined point in time after the pre-pulse, which is optimal for signal-to-noise ratio and/or contrast.

12 Claims, 3 Drawing Sheets

(56) References Cited

U.S. PATENT DOCUMENTS

| | | | | |
|---|---|---|---|---|
| 6,377,045 | B1* | 4/2002 | Van Den Brink | G01R 33/4822 324/307 |
| 7,609,058 | B2* | 10/2009 | Laub | G01R 33/5635 324/307 |
| 8,873,820 | B2* | 10/2014 | Grodzki | G01R 33/4816 382/128 |
| 9,041,394 | B2* | 5/2015 | Umeda | G01R 33/5617 324/307 |
| 9,304,179 | B1* | 4/2016 | Xiao | G01R 33/546 |
| 9,320,454 | B2* | 4/2016 | Grodzki | G01R 33/4816 |
| 2004/0061496 | A1* | 4/2004 | Ookawa | G01R 33/563 324/307 |
| 2008/0012563 | A1* | 1/2008 | Weiss | G01R 33/4824 324/307 |
| 2010/0117644 | A1 | 5/2010 | Nimbargi et al. | |
| 2010/0194390 | A1* | 8/2010 | Kannengiesser | A61B 5/0555 324/309 |
| 2010/0253339 | A1* | 10/2010 | Gross | G01R 33/565 324/309 |
| 2010/0261993 | A1 | 10/2010 | van der Kouwe et al. | |
| 2011/0288398 | A1* | 11/2011 | Park | G01R 33/4816 600/410 |
| 2012/0074938 | A1* | 3/2012 | Grodzki | A61B 5/055 324/309 |
| 2012/0076384 | A1* | 3/2012 | Grodzki | G01R 33/4816 382/131 |
| 2012/0081113 | A1* | 4/2012 | Grodzki | G01R 33/4816 324/309 |
| 2012/0126813 | A1* | 5/2012 | Paul | A61B 5/055 324/309 |
| 2012/0153950 | A1* | 6/2012 | Katscher | G01R 33/4824 324/307 |
| 2014/0091794 | A1* | 4/2014 | Grodzki | G01R 33/4816 324/309 |
| 2014/0103928 | A1* | 4/2014 | Grodzki | G01R 33/4816 324/309 |

OTHER PUBLICATIONS

Heid at al., "Rapid Single Point (RASP) Imaging," SMR, 3rd Annual Meeting (1995), p. 684.

Nielles-Vallespin et al., "3D Radial Projection Technique With Ultrashort Echo Times for Sodium MRI: Clinical Applications in Human Brain and Skeletal Muscle," Magnetic Resonance in Medicine, vol. 57 (2007), pp. 74-81.

Grodzki et al., "Ultrashort Echo Time Imaging Using Pointwise Encoding Time Reduction With Radial Acquisition (PETRA)," Magnetic Resonance in Medicine, vol. 67 (2012), pp. 510-518.

Chamberlain et al., "Quiet T1- and T2-weighted brain imaging using SWIFT," Proc. Intl. Soc. Mag. Reson. Med., vol. 19 (2011), p. 2723.

Brant-Zawadzki et al., "MP RAGE: A Three-dimensional, T1-weighted, Gradient-Echo Sequence—Initial Experience in the Brain," Radiology, vol. 182 (1992), pp. 769-775.

Conklin et al., "High-Contrast 3D Neonatal Brain Imaging with Combined T1- and T2-Weighted MP-RAGE," Magnetic Resonance in Medicine, vol. 59 (2008), pp. 1190-1196.

* cited by examiner

METHOD AND MAGNETIC RESONANCE APPARATUS FOR IMAGE ACQUISITION

BACKGROUND OF THE INVENTION

Field of the Invention

The invention concerns a method for image acquisition with a magnetic resonance device using a magnetic resonance sequence (in particular a PETRA sequence) of the type wherein k-space corresponding to the imaging area is scanned, with a first region of k-space that does not include the center of k-space being scanned radially along a number of spokes emanating from the center of k-space, and wherein at least two phase coding gradients have already been ramped up completely before administration of the excitation pulse; and wherein a second central region of k-space that remains without the first region is scanned in a Cartesian manner (in particular via single point imaging), with a pre-pulse (in particular an inversion pulse to establish a T1 contrast) being radiated before a predetermined number of individual measurements for the purpose of increasing the contrast. The invention also concerns a magnetic resonance apparatus that implements such a method.

Description of the Prior Art

Sequences with ultrashort echo times (thus echo times TE<0.5 ms) offer new fields of application in magnetic resonance imaging. They enable the depiction of substances that are not visible with conventional magnetic resonance sequences (for example spin echo or gradient echo sequences) since their repetition time T2 is markedly shorter than the echo time and their signal has already decayed at the acquisition point in time. Some magnetic resonance sequences with ultrashort echo times are additionally extremely quiet since only extremely small gradient changes are necessary. Examples of such sequences that markedly reduce the noise exposure of the patient are the zTE (zero TE sequence), the WASPI sequence (Water and Fat Suppressed Proton Projection MRI), the SWIFT sequence (Sweep Imaging with Fourier Transformation) and the PETRA sequence (Pointwise Encoding Time reduction with Radial Acquisition).

A number of magnetic resonance sequences with ultrashort echo time have been proposed, for example the radial UTE sequence ("Ultrashort Echo Time", see for example the article by Sonia Nielles-Vallespin, "3D radial projection technique with ultrashort echo times for sodium MRI: clinical applications in human brain and skeletal muscle", Magn. Reson. Med. 2007; 57; Pages 74-81). After a wait time after an excitation pulse, the gradients are thereby ramped up and begun simultaneously with the data acquisition. The k-space trajectory that is scanned in such a manner after an excitation travels radially outward from the center of k-space. Therefore, before the reconstruction of the image data (by means of Fourier transformation) starting from raw data acquired in k-space, these raw data are initially transformed onto a Cartesian k-space grid (for example via regridding).

A further approach in order to enable short echo times is to scan (enter raw data into) k-space at points by detection of the free induction decay (FID) is detected. Such a method is also designated as single point imaging, since essentially only one raw data point in k-space is detected per radio-frequency pulse. An example of such a method for single point imaging is the RASP method ("Rapid Signal Point Imaging", O. Heid. et al, SMR, 3rd Annual Meeting, Page 684, 1995). A raw data point in k-space is thereby read out at the echo time TE at a fixed point in time after the radio-frequency excitation pulse, the phase of which raw data point was coded by gradients which are changed by means of the magnetic resonance device for each raw data point or, respectively, measurement point so that k-space can be scanned point-by-point.

A further shortening of the echo time and of the total acquisition time is enabled by the PETRA sequence, which is described by DE 10 2010 041 446 A1 (corresponding to U.S. Pat. No. 8,887,533) and an article by D. Grodzki et al., "Ultrashort Echo Time Imaging Using Pointwise Encoding Time Reduction With Radial Acquisition (PETRA)", Magnetic Resonance in Medicine 67, Pages 510-518, 2012. These publications are herewith incorporated by reference into the disclosure content of the invention, which concerns the concrete realization of PETRA sequences. In the PETRA sequence, k-space corresponding to the imaging area is read out in two different ways. A first region, which does not include the center of k-space, is scanned by at least two phase coding gradients being initially switched (activated) in respective spatial directions by a gradient system of the magnetic resonance apparatus. Only after reaching the full strength of the switched phase coding gradients is a non-selective radio-frequency excitation pulse radiated by a radio-frequency transmission/reception device of the magnetic resonance apparatus. After a time t1 after the last radiated excitation pulse, echo signals are acquired by means of the radio-frequency transmission/reception device (or an additional, possibly dedicated radio-frequency reception device) and these are stored as raw data points along the radial k-space trajectories (spokes) predetermined by the strength of the phase coding gradients. These steps are repeated until k-space corresponding to the imaging area is read out along radial k-space trajectories in the first region depending on time t1. The switching of the phase coding gradients and the wait until these are ramped up can be further reduced to the echo time, for example in comparison to the UTE sequence. However, a central, spherical region including the center of k-space—the second region of k-space—cannot be scanned in that the phase coding gradients have already been ramped up. It is consequently provided that the second region of k-space (which consequently is not covered in the first region of k-space and which includes the center of k-space) is measured differently, wherein the scanning here takes place in a Cartesian manner, in particular by means of a single point imaging method (for example RASP). Since the raw data acquired in this second portion of the scanning are already situated on a Cartesian k-space grid, while the radially read-out raw data must still be transformed into this (as was already presented above) before image data can be reconstructed from the raw data by means of Fourier transformation, an additional savings of cost and time results.

The contrast of magnetic resonance sequences with ultrashort echo time (in particular thus also the PETRA sequence) is in the range of proton density weighting to T1 weighting. Given constant repetition time and constant flip angle over the measurement, what is known as a steady state develops that determines the precise contrast. In the zTE, WASPI, SWIFT and PETRA sequence, the flip angles are often limited to less than approximately eight to twelve degrees, which leads to a predominantly proton density-weighted contrast given typical repetition times of 3 to 5 ms.

In order to obtain a T1 or also a T2 contrast, it has been proposed to use pre-pulses that are respectively radiated before at least one part of the measurement processes. To save time, it is thus conceivable to apply the pre-pulses only every n repetitions, which (for example) is described in the article "Quiet T1- and T2-weighted brain imaging using SWIFT", Proc. ISMRM 2011, Page 2723 by R. Chamberlain et al.

For the MPRAGE sequence (see for example the article by M. Brant-Zawadzki et al., "MP RAGE: a three-dimensional T1-weighted, gradient-echo sequence—initial experience in the brain", Radiology 182, Pages 769-775, 1992), individual k-space lines are scanned in a Cartesian manner. If pre-pulses are also used here, after the pre-pulse a defined time $T_{VP}$ is initially waited here, whereupon an acquisition duration of $T_{ACQ}$ follows in which a number of $n=T_{ACQ/TR}$ repetitions are measured, wherein TR designates the repetition time (as is typical). After the acquisition duration, a wait time can further be provided before the next pre-pulse is applied. During the wait time, the spins relax, which can possibly be advantageous for the signal-to-noise ratio, but a complete relaxation typically no longer occurs.

This is explained in detail using the example of an inversion pulse for the T1 weighting. In this case, the spins are initially inverted (consequently rotated by a flip angle of 180°) by the pre-pulse formed as an inversion pulse. If excitation pulses that concern a smaller flip angle are now provided in the relaxation (always spaced by the repetition time), a stability magnetization that does not correspond to the maximum transverse magnetization results depending on the relaxation of the respective material, given which stability magnetization the relaxation time is ultimately "stopped" by the excitation pulses, wherein this stability magnetization is different for different materials (for example grey and white brain matter). A T1 weighting results from this.

If the data acquisition is then interrupted for the new pre-pulses, a complete relaxation also does not occur, such that consequently a rotation out of the maximum transverse magnetization does not occur, but rather either a rotation directly out of the stability magnetization or by a value between the maximum transverse magnetization and the stability magnetization. A steady state therefore results after a specific time (a transient event), which means that the curves of the magnetizations are the same given each cycle of pre-pulse and measurement process.

In the MPRAGE sequence measurement (data acquisition) takes place only in the steady state, which has arisen at the beginning of the complete measurement after a few of these cycles (in part already after one cycle). Often a waiting takes place for the duration of provided a pair of these cycles before executing the measurement, in order to not contaminate the measurement with data from the transient event.

A procedure is known to optimize the MPRAGE sequence so that an optimally good contrast—for example between grey and white brain matter—is achieved given an optimally high SNR. In this procedure, an optimized point in time TI after the administration of the pre-pulse is determined, in which an optimally good contrast is provided (for example a clear difference between the transverse magnetization components) but also in which the absolute value (of the transverse magnetization components, for example) is large enough that the signal-to-noise ratio is sufficiently high. A balancing ultimately takes place, from the result of which an optimal point in time TI can be derived that typically is during the relaxation process, before reaching the stability magnetization discussed above.

For the MPRAGE sequence it was then proposed that the k-space lines that are closest to the k-space center, and those that are most decisive for the contrast and the signal-to-noise ratio, be specifically measured at the optimized point in time T1 after the administration of the pre-pulse.

Due to the different principle, this procedure in the MPRAGE sequence cannot be directly transferred to the PETRA sequence.

SUMMARY OF THE INVENTION

An object of the invention to improve the contrast and the signal-to-noise ratio even in a magnetic resonance sequence (in particular the PETRA sequence) that combines radial scanning of k-space and Cartesian scanning of k-space.

This object is achieved in a method of the aforementioned type wherein, according to the invention, the number of spokes to be filled in the radial scanning is selected such that a measurement point charted closest to the center of k-space in the Cartesian coordinate system is measured (filled) at a predetermined point in time after a pre-pulse, which point in time is optimal with regard to the signal-to-noise ratio and/or the contrast.

Typical magnetic resonance sequences of this type—in particular PETRA sequences—have two measurement segments in which, initially, the first region of k-space is measured (radial scan), whereupon the Cartesian scan takes place in a second region of k-space in a further measurement segment. A number of spokes—for example several tens of thousands of spokes—are thereby designated to be filled with data in order to design the back-calculation (regridding) to a Cartesian grid in k-space so as to have as few errors as possible before a reconstruction of the image data from the raw data. The typical procedure (as described above) is that a specific, fixed number of repetitions are measured after each administration of pre-pulse (and a corresponding first wait time $T_{VP}$), which means that the entire measurement process with its $N_{ges}$ measurement processes (repetitions) is subdivided by the pre-pulses into sub-segments, such that at which point in time the center of k-space is measured is ultimately random. The method according to the invention improves this procedure by adapting the described procedure in the MPRAGE sequence to the PETRA sequence, and the characteristics of the PETRA acquisition are optimally utilized. If (as already described) it is assumed that the two measurement segments are present, in accordance with the present invention a targeted, minimal increase or decrease of the number of radial spokes to be measured is determined, in order to shift the point in time at which the center of k-space is measured to the optimal acquisition point in time (as has already been noted with regard to the general description of the prior art). An optimal point in time (defined by a time TI after the pre-pulse) is thus determined during the relaxation after a pre-pulse (as is known in the prior art), and the number of radial spokes is specifically, minimally modified after this specification of the optimal point in time. Decisive advantages result from this, namely stabilization of the contrast, better modulation of the contrast, and an optimal agreement between contrast and signal-to-noise ratio (SNR). The method is applicable to different pre-pulses, in particular also to T2 pre-pulses at desired T2 contrasts.

It would be a "naive" approach to implement the invention by interrupting the normal workflow of the magnetic resonance sequence at the optimal point in time and shift between points from the k-space center. According to the invention this is not preferred because it can lead to larger gradient jumps (discontinuities); that would cause the noise exposure during the sequence to markedly increase, and consequently an advantage of the original magnetic resonance sequence would be lost. Such jumps can also lead to measurement errors. Therefore, the present invention proposes to not, or to minimally, modify the original workflow of the magnetic resonance sequence by means of the radial portion of the magnetic resonance sequence being extended or shortened by a defined proportion.

It is advantageous for additional measurement points near the k-space center to be measured at least near the optimal point in time. In a further embodiment of the present invention, it can consequently be provided that the radial measurement points of the second region that are to be scanned are measured along an acquisition trajectory in k-space such that a defined number (in particular 27, 64 or 125) of measurement points situated closest to the center of k-space are measured first after the optimal point in time. This means that the acquisition trajectory in k-space along which the points of the second region are acquired is adapted in order to be able to measure optimally many center-proximal measurement points as close as possible to the optimal point in time. For example, a spiral-like acquisition trajectory can be used that begins at the measurement point measured in a Cartesian manner nearest the center of k-space (which measurement point in particular lies precisely at the center of k-space) and continues outwardly in a spiral manner so that initially the measurement points situated optimally close to the center are scanned temporally adjacent to the optimal point in time.

It is advantageous to determine an actual number of spokes to be measured from a user specification of the number of spokes to be measured. Because the basic workflow of the complete magnetic resonance sequence is known, in particular with regard to the points in time and the subsequent measurement processes (repetitions), a small (in terms of percentage) correction that shifts the measurement of the k-space center to the optimal point in time can be applied automatically from a number of radial spokes that are predetermined by the system or according to a desire chosen by a user. A correction that is barely detectable or completely undetectable by the user is consequently made that leads to a markedly improved quality of the image acquisition with regard to the contrast and the signal-to-noise ratio.

Proceeding from the specification of the number of spokes, a first number of measurement processes of a repetition time is determined that take place after a pre-pulse before the measurement point measured (in a Cartesian manner) nearest the center of k-space, and a second number of measurement processes is determined that take place after a pre-pulse, before the measurement point measured (in a Cartesian manner) nearest the center of k-space is determined at the optimal point in time. The number of spokes is used (set) that results from the specified number minus the first number, plus the second number. At this point it is further noted that, in general, the same repetition times are typically used over the entire magnetic resonance sequence in order to not contaminate the steady state.

A derivation of this correlation is discussed briefly in the following.

It follows from the number of radial spokes $N_{PA}$ predetermined by the system or selected by the user, and the number of points read out in a Cartesian manner before the readout of the measurement point nearest the center of k-space (designated in the following with $N_K$), that $$FLOOR\{(N_{PA}+N_K)\cdot TR/T_{ACQ}\}$$

pre-pulses were applied before acquisition of the raw data in the center of k-space, wherein $T_{ACQ}$ indicates the acquisition time after each pre-pulse; TR is the repetition time; and the FLOOR function rounds the calculated number down to a whole number. After the pre-pulse (which is provided last before acquisition of the measurement point closest to the center of k-space), $$N_a=N_{PA}+N_K-FLOOR\{(N_{PA}+N_K)\cdot TR/T_{ACQ}\}\cdot T_{ACQ}/TR$$

repetitions have therefore been measured, consequently measurement processes have taken place. Without an adaptation, the center of k-space in this case would be measured at the time $N_a \cdot TR+T_{VP}$, wherein $T_{VP}$ is the wait time after the administration of the pre-pulse.

So that the measurement point nearest the center of k-space is measured at the time TI (thus at the optimal point in time) after the pre-pulse, $$N_{must}=(TI-T_{VP})/TR$$

measurement processes must take place between the pre-pulse and the measurement point nearest the center of k-space. $N_a$ is the first number; $N_{must}$ is second number. In order to satisfy the condition that $N_{must}$ measurement processes take place before the measurement of the center of k-space, as described the number $N_{PA}$ of the radial spokes is either increased or decreased. The condition is satisfied if a number $$N_{new}=N_{PA}+N_{must}-N_a$$

of radial spokes are measured before the beginning of the measurement segment in which the Cartesian scanning takes place. This adaptation minimally modifies the measurement time, and in fact in the millisecond range, but otherwise has no consequences whatsoever for the resolution or the like.

In addition to the method, the invention concerns a magnetic resonance apparatus having a control device configured to operate a data acquisition unit to implement the method according to the invention. Magnetic resonance apparatuses are fundamentally known in the prior art and generally are designed in order to use a number of magnetic resonance sequences in order to acquire images. According to the invention, the control device of such a magnetic resonance apparatus is designed to produce the automatic modification of the number of radial spokes to be acquired in order to cause the center of k-space to be measured (filled with raw data) at an optimal point in time so as to thus achieve an improved image quality. All statements with regard to the method according to the invention apply analogously to the magnetic resonance apparatus according to the invention, with which the cited advantages can consequently also be achieved.

DESCRIPTION OF THE PREFERRED EMBODIMENTS

Figure 1:
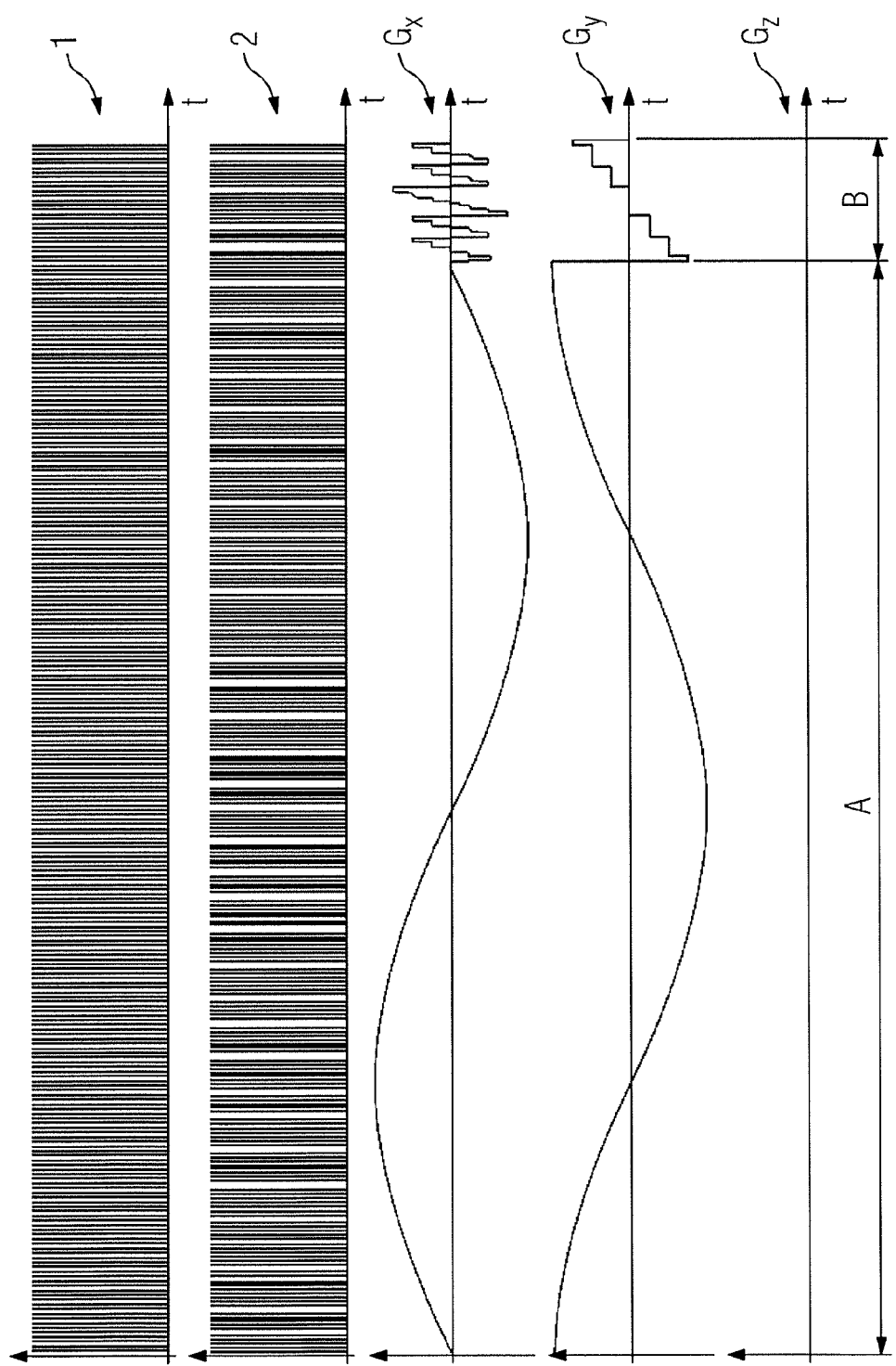
FIG. 1 shows a PETRA sequence according to the prior art for the acquisition of k-space corresponding to an imaging area.

FIG. 1 shows the workflow of a PETRA sequence as a magnetic resonance sequence, as is known in the prior art (for example DE 10 2010 041 446 A1, corresponding to U.S. Pat. No. 8,887,533), and that can be used for image acquisition in a magnetic resonance device. The first line in FIG. 1 shows the radiated radio-frequency excitation pulses 1; the second line shows the associated readout time periods 2. The excitation pulses 1 are respectively repeated at an interval of a repetition time TR which remains constant across the entire sequence. In the present exemplary embodiment, two phase coding gradients $G_x$ and $G_y$ are switched, such that a coding in the third direction (the slice direction, here the z-direction) is foregone ($G_z$=0).

If scanning takes place both in a first measurement segment A in which a first region of k-space is scanned radially along spokes and in a second measurement segment B in which the second region of k-space (that is not included by the first region) which includes the center of k-space, and the gradients are changed only very slightly (in particular continuously in the measurement segment A) so-that an extremely quiet acquisition of the raw data is possible.

Figure 5:
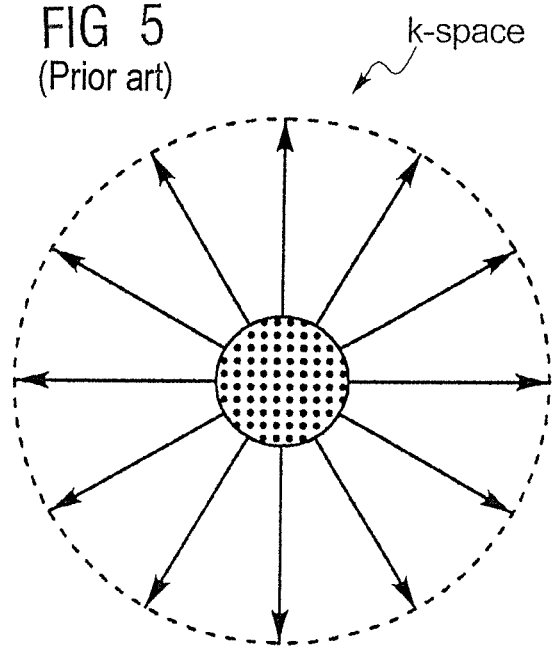
FIG. 5 schematically illustrates the manner of entering acquired magnetic resonance data into k-space according to the known PETRA sequence.

FIG. 5 shows the manner by which acquired magnetic resonance data are entered into the aforementioned first and second regions of k-space, with the data being entered into the second region of k-space radially along spokes. FIG. 5 illustrates this known manner of k-space data entry according to the PETRA sequence. The method and apparatus according to the invention are for the purpose of automatically determining the number of spokes in k-space along which data are to be entered in the first region.

Figure 2:
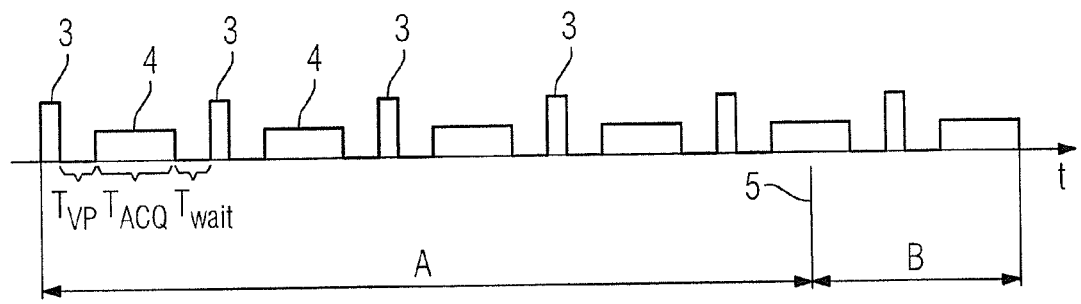
FIG. 2 is a flowchart of a measurement with the administration of pre-pulses.

In the exemplary embodiment, a case is considered in which an inversion pulse to establish a T1 contrast between white and grey brain matter is provided as a pre-pulse for a defined number of repetitions, such that the entirety of the repetitions (measurement processes) are distributed to multiple pre-pulses as they result via combinations of excitation pulses and readout times, as is schematically shown in FIG. 2. The pre-pulses 3 are schematically shown with the subsequent measurement time periods 4. In the following, the wait time before the measurement can be begun after a pre-pulse 3 is designated with $T_{VP}$, the measurement duration in a measurement time period 4 (which is a multiple of the repetition time TR) is designated with $T_{ACQ}$, and the optional further wait time period before the next pre-pulse 3 is designated with $T_{wait}$. Given the regular use of the pre-pulses 3 and the respective identically long times $T_{VP}$, $T_{ACQ}$ and $T_{wait}$, a steady state results in which the magnetization curve is the same for each cycle of pre-pulse 3 and measurement time period 4. Such a magnetization curve is shown in FIG. 3 and is discussed in detail in the following; however, it is initially noted that—under the cited circumstances—a point in time 5 dependent on the number of radial spokes to be acquired results, at which point in time 5 the second measurement segment B begins.

Figure 3:
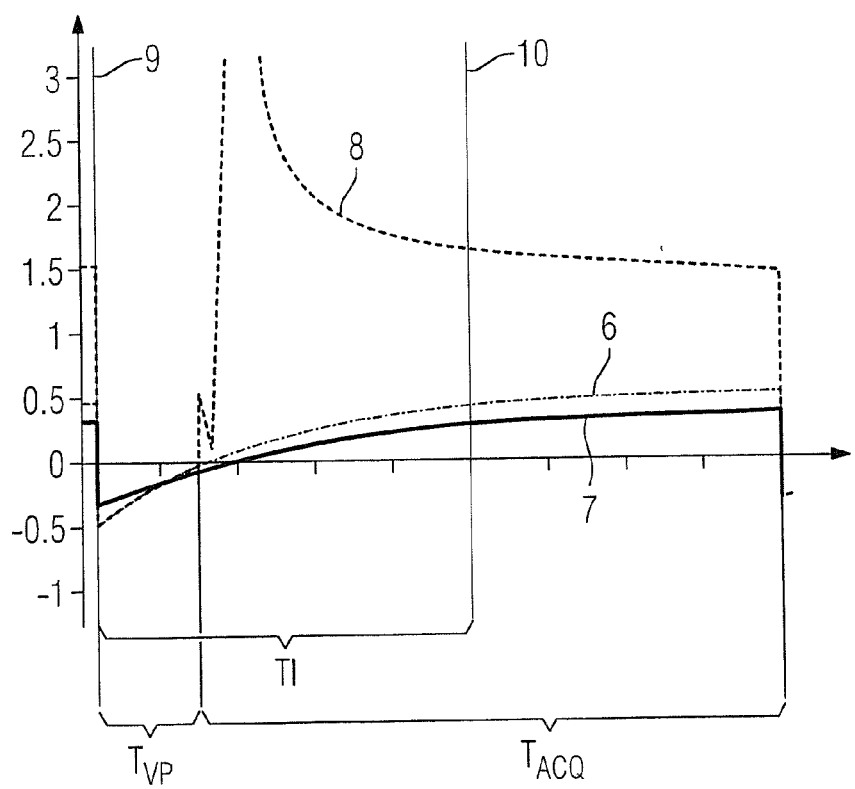
FIG. 3 shows the curve of transverse magnetization after the administration of a pre-pulse in the steady state.

FIG. 3 shows the magnetization curve for the materials to be differentiated (here white and grey brain matter) in a cycle, wherein the curve 6 denotes the white brain matter, the curve 7 denotes the grey brain matter and the curve 8 shows the ratio of the transverse magnetizations (shown here) of white brain matter to grey brain matter. This curve of the transverse magnetizations is the same for each cycle (steady state).

The inversion pulse (pre-pulse) 3 was clearly provided at a point in time 9 so that the transverse magnetizations have been flipped by 180°. The transverse magnetizations then begin to relax, wherein again the wait times $T_{VP}$ and $T_{ACQ}$ are shown. The influences of the respective excitation pulses 1 (which are due to only small flip angles) are not apparent due to the scaling. However, these lead to the situation that a complete relaxation cannot occur.

Clearly, quite a high ratio exists after the beginning of the acquisition time period 4, but, the values of the transverse magnetization are low, such that a high signal-to-noise ratio is present. While the values of the transverse magnetization increase, the curve 8 indicates, however, that the ratio decreases; the contrast is thus lower. An optimal point in time 10 (described by the time TE at which the best compromise is present) can be determined deliberately between these effects (thus contrast and signal-to-noise ratio).

The method according to the invention provides an automatic adaptation of the number of radial spokes to be acquired in measurement segment A, such that the center of k-space (specifically the measurement point nearest the center of k-space) is measured at a point in time 10 in measurement segment B (in which the Cartesian scanning takes place) because this has the greatest influence on the contrast and the signal-to-noise ratio. Repetitions are thus added or removed relative to a system or user setting, which occurs automatically, namely by a control device of a magnetic resonance device, such that this condition is provided. Because the number of radial spokes to be acquired (for example as it is provided by a user) is most often extremely large, it is a minimal change that has no influence whatsoever on the desired resolution and the like.

Concretely, the formula presented above is thereby used, according to which the new number of spokes to be measured—$N_{new}$—automatically results as $$N_{new} = N_{PA} + N_{must} - N_a.$$

In addition to this variation, the k-space trajectory of the Cartesian measurement segment B is also slightly modified in that the central $n^3$ points (for example for n=3, 4 or 5) that are nearest the k-space center are singled out and are measured along a preferred, spiral-like k-space trajectory so that they are measured according to their proximity to the k-space center after the optimal point in time 10. The measurement points that are most important for the contrast and signal-to-noise ratio are thus measured in the immediate surroundings of the optimal point in time 10. Additional gradient jumps barely arise due to this modification, which means that the magnetic resonance sequence remains quiet.

Figure 4:
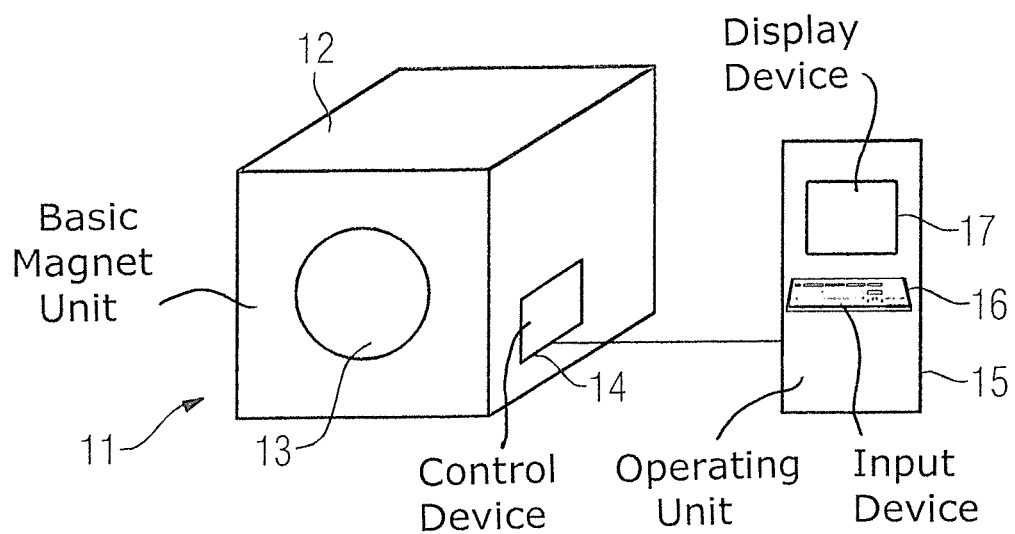
FIG. 4 schematically illustrates a magnetic resonance device according to the invention.

FIG. 4 shows a basic drawing of a magnetic resonance device 11 according to the invention. As is known, this has a basic magnet unit 12 in which a patient can be driven through a patient receptacle 13. The patient receptacle 13 can surround a radio-frequency transmission/reception device, for example a body coil (not shown in detail here for clarity), and the gradient coils can be provided.

The operation of the magnetic resonance device 11 is controlled via a control device 14 which realizes the PETRA magnetic resonance sequence with the set sequence parameters (in particular the modified number of radial spokes) in the image acquisition. The control device 14 is connected with an operating unit 15 which has a display device 17 and an input device 16. Adjustable sequence parameters can hereby be set—for example a number of radial spokes to be acquired—according to the desire of a user.

The control device 14 is designed to implement the method according to the invention, meaning that it automatically adapts the number of radial spokes to be acquired so that the center of k-space is measured at an optimal point in time.

Although modifications and changes may be suggested by those skilled in the art, it is the intention of the inventor to

I claim as my invention:

1. A magnetic resonance (MR) apparatus comprising:
   an MR data acquisition unit;
   a computer configured to operate the MR data acquisition unit according to an MR data acquisition sequence in which raw MR data acquired from an imaging area of an examination subject are entered into an electronic memory organized as k-space, by entering said raw MR data into a first region of k-space, which does not include a center of k-space, radially along a number of straight spokes emanating from the center of k-space, and wherein at least two phase coding gradients are completely ramped up before exciting nuclear spins in the examination subject, and by entering said raw MR data into a second, central region of k-space, that remains without the first region, in a Cartesian manner and wherein a contrast-increasing pre-pulse is radiated before a predetermined number of individual acquisitions of said raw MR data;
   said computer being configured to automatically set a number of said spokes to cause a data entry point, defined in a Cartesian manner, nearest to the center of k-space to be filled with said raw MR data at a predetermined point in time that is optimized with regard to at least one of signal-to-noise ratio and said contrast in an MR image reconstructed from said raw MR data; and
   said computer being configured to make k-space, with said raw MR data entered therein according to the set number of spokes, available as a data file at an output of said computer in a format for further processing into image data.

2. A method for automated specification of a protocol for operating a magnetic resonance (MR) data acquisition unit in order to acquire raw MR data from an examination subject, said method comprising:
   from a computer, accessing a data file from a memory that comprises parameters and commands for operating an MR data acquisition unit from the computer according to an MR data acquisition sequence in which MR data acquired from an imaging area of an examination subject are entered into an electronic memory organized as k-space, by entering said MR data into a first region of k-space, which does not include a center of k-space, radially along a number of straight spokes emanating from the center of k-space, and wherein at least two phase coding gradients are completely ramped up before exciting nuclear spins in the examination subject, and by entering said raw MR data into a second, central region of k-space, that remains without the first region, in a Cartesian manner and wherein a contrast-increasing pre-pulse is radiated before a predetermined number of individual acquisitions of said raw MR data;
   in said computer, automatically setting a number of said spokes so as to cause a data entry point, defined in a Cartesian manner, nearest to the center of k-space to be filled with said raw MR data at a predetermined point in time that is optimized with regard to at least one of signal-to-noise ratio and said contrast in an MR image reconstructed from said raw MR data; and
   making the data file, with the set numbers of spokes available at an output of the computer in a format forming a protocol for operating the MR data acquisition unit.

3. A method as claimed in claim 2 comprising:
   making a manual entry into said computer designating a designated number of said spokes; and
   in said computer, setting said number of spokes using said designated number of spokes as a starting number.

4. A method as claimed in claim 3 comprising:
   in said computer, determining a first number of repetitions of acquisition of said raw MR data that occur after said pre-pulse and before entry of said raw MR data at said optimized point in time;
   determining a second number of repetitions of acquisition of said raw MR data that occur after said pre-pulse and before entry of said raw MR data into said data entry point before optimizing said point in time; and
   in said computer, determining said number of spokes as said designated number minus said first number and plus said second number.

5. A method as claimed in claim 2 wherein said MR data acquisition sequence is a PETRA sequence.

6. A method for operating a magnetic resonance (MR) data acquisition unit in order to acquire raw MR data from an examination subject, said method comprising:
   operating an MR data acquisition unit from a computer according to an MR data acquisition sequence, specified in said computer, in which raw MR data acquired from an imaging area of an examination subject are entered into an electronic memory organized as k-space, by entering said raw MR data into a first region of k-space, which does not include a center of k-space, radially along a number of straight spokes emanating from the center of k-space, and wherein at least two phase coding gradients are completely ramped up before exciting nuclear spins in the examination subject, and by entering said raw MR data into a second, central region of k-space, that remains without the first region, in a Cartesian manner and wherein a contrast-increasing pre-pulse is radiated before a predetermined number of individual acquisitions of said raw MR data;
   in said computer, automatically setting a number of said spokes so as to cause a data entry point, defined in a Cartesian manner, nearest to the center of k-space to be filled with said raw MR data at a predetermined point in time that is optimized with regard to at least one of signal-to-noise ratio and said contrast in an MR image reconstructed from said raw MR data; and
   making k-space, with said raw MR data entered therein according to the set number of spokes, available as a data file at an output of said computer in a format for further processing into image data.

7. A method as claimed in claim 6 comprising:
   making a manual entry into said computer designating a designated number of said spokes; and
   in said computer, setting said number of spokes using said designated number of spokes as a starting number.

8. A method as claimed in claim 7 comprising:
   in said computer, determining a first number of repetitions of acquisition of said raw MR data that occur after said pre-pulse and before entry of said raw MR data at said optimized point in time;
   determining a second number of repetitions of acquisition of said raw MR data that occur after said pre-pulse and before entry of said raw MR data into said data entry point before optimizing said point in time; and in said computer, determining said number of spokes as said designated number minus said first number and plus said second number.

9. A method as claimed in claim 6 wherein said MR data acquisition sequence is a PETRA sequence.

10. A method as claimed in claim 6 comprising:

entering data at data entry points in said second region along a trajectory in k-space that causes a defined number of data entry points in said second region, that are situated closest to the center of k-space, to have said raw MR data entered therein first, after said optimized point in time.

11. A method as claimed in claim 6 comprising radiating said pre-pulse as an inversion pulse that establishes a T1 contrast.

12. A method as claimed in claim 6 comprising entering said raw MR data into said second region of k-space in said Cartesian manner by single point imaging.

* * * * *